United States Patent [19]

Li

[11] 4,189,426

[45] Feb. 19, 1980

[54] RECOMBINANT HORMONAL COMPOSITIONS AND METHOD

[75] Inventor: Choh H. Li, Berkeley, Calif.

[73] Assignee: Hoffmann-La Roche, Inc., Nutley, N.J.

[21] Appl. No.: 938,278

[22] Filed: Aug. 31, 1978

Related U.S. Application Data

[63] Continuation-in-part of Ser. No. 892,571, Apr. 3, 1978, abandoned, which is a continuation-in-part of Ser. No. 842,437, Oct. 14, 1977, abandoned, which is a continuation of Ser. No. 675,668, Apr. 12, 1976, abandoned.

[51] Int. Cl.$^2$ ............... C07C 103/52; A61K 37/00
[52] U.S. Cl. ............... 260/112.5 R; 424/177
[58] Field of Search ............... 260/112.5 R; 424/177

[56] References Cited

U.S. PATENT DOCUMENTS

| | | | |
|---|---|---|---|
| 3,475,534 | 10/1969 | Fenichel et al. | 260/112.5 R |
| 3,853,832 | 12/1974 | Li | 260/112.5 R |
| 3,907,765 | 9/1975 | Wang | 260/112.5 R |
| 4,056,520 | 11/1977 | Sonenberg et al. | 260/112.5 R |

OTHER PUBLICATIONS

Arch. Biochem. and Biophysic., 146, 233-236 (1971).
J. Org. Chem., 40, No. 9, 1227-1234 (1975).
J. Med. Chem. 18, No. 2 (1975), 124-126.
Endocrinol. 93, (1973), 848-857, 858-865, 866-873.
The Endocrine Society, 1970, 112.
Endocrinology 94, 1974, 883-891.
Endocrinology 96, 625-636.
Nature 237, 1972, 433-439.
Li, et al., Chem. Abst. 85, 1976, p. 186915K.

*Primary Examiner*—Delbert R. Phillips
*Attorney, Agent, or Firm*—Jon S. Saxe; George M. Gould

[57] ABSTRACT

Non-covalent complementation of peptide hormonal fragments produces a recombinant with the hormonal activity of the native hormone. The fragments employed can be natural, synthetic or mixed natural-synthetic origin and can contain less than the total amino acid sequence of the native hormone or fragments derived from related hormones. In a preferred embodiment the human growth hormone (HGH) fragments [Cys(Cam)$^{53}$-HGH-(1-134)] and [Cys(Cam)$^{165,182,189}$-HGH-(141-191)] undergo non-covalent complementation to yield a recombinant having full growth-promoting and prolactin potency of the native human growth hormone.

18 Claims, No Drawings

RECOMBINANT HORMONAL COMPOSITIONS AND METHOD

RELATED APPLICATIONS

This application is a continuation-in-part of copending application Ser. No. 892,571, filed Apr. 3, 1978, now abandoned, which was a continuation-in-part of application Ser. No. 842,437, filed Oct. 14, 1977 now abandoned, which was a continuation of application Ser. No. 675,668, filed Apr. 12, 1976 and now abandoned.

BACKGROUND OF THE INVENTION

It has been known that peptide fragments derived from native enzymes are capable of recombination by non-covalent interaction to regenerate enzymic activity. See for example Anfinsen and Scheraga, Adv. Prot. Chem. 29, 205(1975) and Zabin and Willarejo, Ann. Res. Biochem. 44, 295 (1975).

Singh et al, Endocrinology 94, 883 (1974) disclose the treatment of human growth hormone with human plasmin so as to produce a modified human growth hormone missing residues 135–140 from the large disulfide loop of the protein.

Blake and Li, Int. J. Peptide Protein Res. 11, 315 (1978) have described the synthesis of [Nle$^{170}$, Ala$^{165, 182, 189}$]-HGH-(145-191), [Nle$^{170}$, Ala$^{165,182,189}$]-HGH-(140-191), and [Lys$^{135, 136, 138}$, Glu$^{137, 139}$, Nle$^{170}$, Ala$^{165, 182, 189}$]-HGH-(135-191). The non-covalent complemenation of the first two named compounds with [Cys(Cam)$^{53}$]-HGH-(1-34) produce recombination HGH compositions having full biological and immunological activity is described by Li et al., Biochem. Biophys. Res. Com. 82(1), 217 (1978).

The non-covalent complementation of the prolactin (PRL) inactive fragments PRL-(1-53) and PRL-(54-199) yields a recombinant having a low but measurable biological activity and the full immunoreactivity as well as circular dichroism spectra of the native hormone. See Birk and Li, Proc. Natl. Acad. Sci. U.S.A. 75(5)₣2155 (1978).

DESCRIPTION OF THE INVENTION

The present invention relates to novel recombinant compositions obtained by non-covalent complementation of peptide hormonal fragments. These compositions are surprisingly found to exhibit up to the full hormonal activity of the native peptide hormone.

The source of the fragments employed in the practice of the present invention is not critical. Thus it is possible to utilize fragments derived by enzymatic digestion of natural hormones, synthetically produced fragments having the same or analogous amino acid sequence of the corresponding portion of the natural hormone or mixtures of naturally derived and synthetically produced fragments. It has also been found possible to combine fragments from related hormones such as human growth hormone and human choriomammotropin hormone also known as human chorionic somatomammotropin (HCS). Generally, it is preferred that the peptide hormones employed herein contain a single chain and have a molecular weight of greater than about 5,000.

In cases wherein the natural peptide hormone selected has disulfide bridge bonds it is possible to reduce such bonds in a manner known per se, i.e., by procedures described in detail by Li and Graf. Proc. Nat. Acad. Sci. U.S.A. 71, 1197 (1974) and then to derivatize the free cysteinyl sulphydryl groups such as for example by carboxamidomethylation with iodoacetamide to introduce the carbamoylmethyl (Cam) group prior to enzymatic digestion. Similarly, the synthetically produced peptide fragments containing cystein moieties may be derivatized in like manner.

The length of the respective fragments utilized will of course depend on the nature of the peptide hormone whose activity it is desired to produce by non-covalent complementation. This can be conveniently determined in each case by ad hoc experimentation utilizing fragments of varying chain lengths, subjecting them to complementation and measuring either the circular dichroism spectra or the immunoreactivity to a hormone specific antibody of the recombinant. Comparison of the resulting spectra or antibody binding curve with that obtained from the native peptide hormone will provide the indication when the chain length of the fragments are sufficient to provide proper identity with the conformation of the native hormone.

Recombination can be readily carried out by allowing approximately equimolar amounts of the desired fragments to react non-covalently in an aqueous buffered solution having a pH in the range of from 6 to 10 preferably about 8.4. A preferred buffer for this purpose is pH 8.4 tris buffer. The temperature at which the complementation is carried out is not narrowly critical and can conveniently be in the range of from about 0 to 10° C. The reaction medium can also contain a minor amount of a $C_{1-4}$ lower alkanol, i.e., n-butanol, to enhance solubility of the fragments. Completion of the reaction can be determined most readily by observing the loss of turbidity until a final clear solution is obtained or alternatively by following the circular dichroism spectra of the solution.

The recombinants obtained by the above procedure are stable to conventional purification procedures utilized in peptide chemistry. Thus, for example, recombinants may be readily purified after reaction by concentration utilizing ultrafiltration followed by exclusion chromatography on Sephadex G-100 using tris buffer (pH 8.2).

In a preferred embodiment a recombinant composition is obtained having the equivalent biological activity of natural human growth hormone. Such recombinant composition is preferably prepared by the non-covalent complementation of two peptide fragments [Cys(Cam)$^{53}$-HGH-(1-134)] and [Cys(Cam)$^{165,182,189}$-HGH-(141-191)]. These fragments are known compounds and are readily prepared by treatment of human growth hormone with the enzyme plasmin. This enzyme is known to cleave the Arg-Thr (positions 134–135) and the Lys-Gln (positions 140–141) bonds of the hormone thereby producing essentially the fragments HGH (1-134), HGH (135-140) and HGH (141-191). This cleavage is not affected by the prior reduction and carboxamidomethylation of the hormone. Separation of the two desired fragments from the hexapeptide is readily accomplished by conventional procedures.

In an alternative embodiment, the known synthetic COOH-terminal fragment [Cys(Cam)$^{165, 182, 189}$-HGH-(141-191)] can be employed in the complementation reaction in equivalent manner as the fragment of the same sequence derived above by plasmin digest of reduced-carbamidomethylated human growth hormone.

The growth-promoting activity as determined by the rat tibia test and the prolactin activity as determined by the local crop-sac assay in the pigeon for either of the fragments [Cys(Cam)$^{53}$-HGH-(1-134)] and [Cys(Cam)$^{165, 182, 189}$HGH-(141-191)] is only a very small fraction of the comparative biological activities of the native human growth hormone whereas the recombinant formed by non-covalent complementation of the same two fragments yields growth-promoting activity of equivalent potency as the native hormone.

In a further aspect of this invention, recombinant hormones having growth-promoting activity are obtained by submitting fragments derived from HGH and HCS to complementation reaction. It has been found, for example that the HGH fragment Cys (Cam)$^{53}$-HGH-(1-134) is capable of reacting noncovalently with Cys (Cam)$^{165, 182, 189}$-HCS-(141-191) to produce a recombinant with significant growth-promoting activity and nearly full immunoreactivity against the antiserum to HGH.

Similarly the fragments Cys(Cam)$^{53}$-HCS-(1-133) and Cys(Cam)$^{165, 182, 189}$-HGH-(141-191) can be reacted non-covalently to produce a recombinant which has measurable growth promoting activity but at a reduced level of potency than the aforesaid recombinants. It should be noted that the two HCS fragments used above exhibit no independent growth-promoting activity.

It is evident from the foregoing that the present invention provides compositions that will function in a manner completely analogous to that of the corresponding natual hormone.

While human growth hormone has been given as a preferred embodiment of a target hormone for the recombinants of the present invention it should be understood that the activity of any other peptide hormone, particularly a single chain peptide hormone having a molecular weight over 5,000 could be produced by proper selection of the fragment components and reaction thereof by non-covalent complementation in the manner described above. Thus, for example non-covalent complementation of fragments of the peptide hormone prolactin (PRL) affords a composition having the full immunoreactivity and measurable biological activity of the parent hormone although the fragments themselves are devoid of immunological or biological prolactin activity. Generally, as a matter of convenience, it is preferred to utilize two fragments in the complementation reaction. However, it is possible in appropriate circumstances and depending on the identity and nature of the hormonal activity desired to employ three or even more fragments.

EXAMPLE 1

Human Growth Hormone Recombinant By Complementation Of Plasmin Digests Fragments A mixture was prepared by adding 13.11 mg (0.87 μmol) of [Cys(Cam)$^{53}$-HGH-(1-134)] which had been repurified by gel filtration on Sephadex G-100 in 0.1 M NH$_4$HCO$_3$ of pH 8.2 to 5.4 mg (0.89 μmol) of (Cys(Cam)$^{165, 182, 189}$-HGH-(141-191) in 10 ml of pH 8.4 tris buffer (0.1 M, 2% butanol). The turbid solution was kept at room temperature (23° C.) for 5 hours and then transferred to the refrigerator (2° C.). After 240 hours, the solution appeared to have become clear.

The fragment mixture was concentrated to 1 ml by ultrafiltration through an amicom UM-Z membrane and was then submitted to exclusion chromatography on a 1.5×5.8 cm column of Sephadex G-100 in 0.1 M tris buffer (pH 8.2). Approximately 25% of the protein appeared in a distinct peak (designated as fraction IV) with a Ve/Vo ratio of 2.12. This is precisely the elution position of intact PL-HGH on the same column. It is especially noteworthy that no detectable protein was found at a Ve/Vo ratio of 2.9–3.1, the elution position expected for the free COOH-terminal fragment.

The circular dichroism (CD) spectra of the fraction IV material before purification presents an interesting feature in the appearance of a weak negative band around 298 nm. This band has previously been assigned to the Trp-86 residue in the NH$_2$-terminal. The negative sign of this indole dichroism is characteristic of the conformation of the free fragment and is in sharp contrast to the positive indole dichroism at 292 nm, characteristic of the conformation of intact reduced-alkylated PL-HGH or native HGH. However, it is observed that in the spectrum of this incubation mixture, the negative band is not as intense as it would be in a pure sample of the NH$_2$-terminal fragment suggesting that the mixture contains overlapping contributions from both positively and negatively dichronic indole groups. The CD spectra of this same sample in the far-UV region indicates an average α-helix content of 45–50% compared to a value of 55% for natural human growth hormone.

The CD spectrum of the purified recombinant fraction IV was compared with the spectrum of a freshly thawed undissociated sample of intact, reduced-carboxamidomethylated PL-HGH. The spectrum of the former material in the region of side-chain absorption was not significantly different from that of intact reduced-carbamidomethylated PL-HGH. The complete equivalence of the positive indole dichroism at 292 nm in these two samples was particularly noteworthy. The far-UV spectrum of fraction IV indicates that this material possibly contains a slightly higher content of α-helix ($\approx 60\%$) than either reduced-carbamidomethylated PL-HGH or native HGH.

EXAMPLE 2

Biological Activity of HGH Recombinant

The growth-promoting activity of PL-HGH, the unpurified recombinant of Example 1 (fraction IV), [Cys(Cam)$^{53}$-HGH-(1-134)], [Cys(Cam)$^{165, 182, 189}$-HGH-(141-191)] and saline control were determined by the rat tibia test of Greenspan et al, Endocrinology 45, 455 (1949) and by the local crop-sac assay in the pigeon according to Lyons, Proc. Soc. Exp. Biol. 35, 645 (1937) and Nicoll, Endocrinology 80, 641 (1967).

Comparative results with the unpurified recombinant are summarized in Table 1 below:

Table 1

Prolactin and Growth-Promoting Activities of the Recombinant Before Purification and the Fragments of HGH

| Preparation | Pigeon crop-sac assay | | Rat tibia assay | |
|---|---|---|---|---|
| | Total Dose (nmol) | Response* | Total Dose (nmol) | Response † |
| PL-HGH | 0.093 | 24.6 ± 0.8 | 0.93 | 241.0 ± 2.4 |
| | 0.279 | 28.8 ± 1.7 | 2.79 | 267.2 ± 7.7 |

Table 1-continued

Prolactin and Growth-Promoting Activities of the Recombinant Before Purification and the Fragments of HGH

| Preparation | Pigeon crop-sac assay Total Dose (nmol) | Response* | Rat tibia assay Total Dose (nmol) | Response† |
|---|---|---|---|---|
| | 0.48‡,§ | 16.8 ± 0.7 | 2.27**,†† | 252.5 ± 10.2 |
| | 1.44 | 20.7 ± 1.4 | 6.81 | 281.2 ± 6.4 |
| Cys(Cam)$^{53}$-HGH-(1-134) | 0.65¶ | 9.6 ± 1.8 | 3.26‡‡ | 207.2 ± 1.5 |
| | 1.95 | 12.4 ± 2.7 | 9.78 | 235.5 ± 1.5 |
| Cys(Cam)$^{165,182,189}$-HGH-(141-191) | 20.3 | 13.4 ± 1.2 | 9.78 | 186.7 ± 4.4 |
| Saline | 0 | 10.5 ± 0.2 | 0 | 176.5 ± 4.5 |

*Dry mucosal weight in mg; mean ± standard error; four birds in each group.
† Tibia width in micra; mean ± standard error; four animals in each group.
‡ Relative potency to PL-HGH, 23% with a confidence limit of 0.3–62 and λ = 0.27.
§ Relative potency to Cys(Cam)$^{53}$-HGH-(1-134), approximately 947% with λ = 0.46.
¶ Relative potency to PL-HGH, less than 1%.
** Relative potency to PL-HGH, 60% with a confidence limit of 40–153 and λ = 0.24.
†† Relative potency to Cys(Cam)$^{53}$-HGH-(1-134), 828% with a confidence limit of 441–3077 and λ = 0.17.
‡‡ Relative potency to PL-HGH, 8% with a confidence limit of 4–12 and λ = 0.12.

It may be seen in Table 1 that the solution containing the two fragments before purification had restored growth-promoting activity from 8% to 60% when compared with the potency of the 134 residue in the tabia test. At the dose tested the potency of the 51 residue fragment was about nil. The regeneration of lactogenic activity was also evident in the pigeon crop-sac assay.

The biological activities of the purified recombinant of Example 1 (fraction IV) are summarized in Table 2 below:

Table 2

Prolactin and Growth-Promoting Activities of the Recombinant Obtained by Noncovalent Interaction of the Two Fragments of HGH

| Preparation | Pigeon crop-sac assay Total Dose (nmol) | Response* | Rat tibia assay Total Dose (nmol) | Response † |
|---|---|---|---|---|
| PL-HGH | 0.093 | 18.5 ± 0.7 | 0.47 | 216.8 ± 2.6 |
| | 0.279 | 25.0 ± 2.1 | 1.40 | 261.3 ± 2.2 |
| Recombinant ‡ | 0.093 § | 19.2 ± 0.8 | 0.47 ¶ | 223.8 ± 10.8 |
| | 0.279 | 24.6 ± 0.8 | 1.40 | 257.8 ± 10.4 |
| Saline | 0 | 10.7 ± 0.2 | 0 | 155.3 ± 4.7 |

*Dry mucosal weight in mg; mean ± standard error; four birds in each group.
† Tibia width in micra; mean ± standard error; four animals in each group.
‡ Fraction IV, see Figure 2.
§ Relative potency to PL-HGH, 102% with 95% confidence limit of 59–176 and λ = 0.22.
¶ Relative potency to PL-HGH, 108% with 95% confidence limit of 70–158 and λ = 0.15.

In comparison with the activities of PL-HGH, the recombinant had full growth-promoting and prolactin potency. It is significant that the prolactin activity of the purified recombinant is restored from less than 1% to 100% of PL-HGH potency as seen in Tables 1 and 2.

EXAMPLE 3

Recombinant Containing Synthetic [Cys(Cma)$^{165, 182, 189}$-HGH-(141-191)]

In analogous manner to the procedure disclosed in Example 1 synthetic COOH-terminal fragment [Cys(Cam)$^{165, 182, 189}$-HGH-(141-191)] prepared by the procedure of Blake and Li, Int. J. Prot. Peptide Res. 7, 495 (1975) was reacted by non-convalent complementation with [Cys(Cam)$^{53}$-HGH-(1-134)] obtained by enzymatic digestion of reduced-carboxamidomethylated HGH. After purification by ultrafiltration and exclusion chromatography, the purified recombinant exhibited equivalent potency as the native HGH in both the tibia test and pigeon crop-sac assay.

EXAMPLE 4

Materials and Methods

Human choriomammotropin hormone (HCS) was obtained as previously described by Li, Ann. Sclavo (Siena) 12, 651 (1970). Highly purified human plasminogen (19 casein units per mg of proenzyme) was activated streptokinase (Calbiochem(as described by Robbins and Summaria, Methods in Enzymology, 19, 184 (1970). HCS was digested by plasmin in 0.05 M ammonium acetate buffer, pH 8.0, with an enzyme to hormone ratio of 1:100 (w/w) at 37° C. for 20 hr. The digest was submitted to purification by gel filtration on Sephadex G-75 and G-100. The reduction and alkylation of the disulfide bridges were carried out as described by Li and Graf, Proc. Natl. Acad. Sci. U.S.A., 73, 1476 (1974) except that 5 M quinidine hydrochloride was used instead of 8 M urea during reduction. After removal of excess reagents by gel filtration on Sephadex G-15 in 0.01 M NH$_4$HCO$_3$, the plasmin fragments were separated and purified by exclusion chromatography on Sephadex G-50 and G-100.

Ultraviolet spectra were obtained on a Beckman DK-2A recording spectrophotometer, using marked pairs of far ultraviolet silica cuvettes. The optical path for all spectra was 1.00 cm. Absorption in the range 340–360 nm, attributed to light scattering, was corrected. Circular dichroism spectra were obtained on a Cary Model 60 spectropolarimeter equipped with a Model 6002 circular dichroism attachment. The instrument was calibrated with D-10-camphorsulfonic acid (Eastmant Organic Chemicals) as recommended by the manufacturers. All spectra were taken at 27° in a 1.00 mm path-length cell. Mean residue molecular ellipticities were calculated using a value of 115 for the mean residue weight. Other calculations were preformed as previously described by Bewley et al. Biochemistry, 8, 4701 (1969). Molecular weight estimates were obtained by a comparison of the mobility of proteins of known molecular weight in polyacrylaminde gels containing SDS.

Amino acid compositions of acid and carboxypeptidase hydrolysates were determined in an automatic amino acid analyzer (model 120B, Beckman Instruments). For the analysis of tryptophan, the methanesulfonic acid hydrolysates were used. Amino-terminal residue and sequence analyses were preformed by the dansyl-Edman procedure. Isoelectric focusing was carried out in 8 M urea. Prolactin activity was estimated by the pigeon crop-sac assay. Microcomplement fixation experiments were performed with rabbit antisera to HCS. The gel-double-diffusion technique of Ouchterlony was done using 1% agar in 0.01 M phosphate buffer of pH 7.5.

Results

A 20 hr plasmin digest of HCS (100 mg) was separated into at least four components on Sephadex G-75 in 20% acetic acid with the yield of 75 mg main component. After it was further purified on Sephadex G-100 in 0.01 M NH$_4$HCO$_3$ of pH 8.4, the recovered material was submitted to reduction and alkylation and the product was resolved into two components by gel filtration on Sephadex G-50 in 10% acetic acid. The isolated components (designated N and C) were chromatographed on Sephadex G-100. From 100 mg HCS, a yield of highly purified N and C were 31 mg and 8 mg, respectively.

Amino acid composition of N and C, as summarized in Table 3, indicated that N is the NH$_2$-terminal 133 amino-acids fragment and C the COOCH terminal 141–191 fragment of the HCS molecule. Amino and carboxyl terminal residue analyses were consistent with this conclusion. In addition, NH-terminal sequence of N was found to be: H-Val-Glx-Thr-Val. Amino acid analyses of carboxypeptidase A/B digests of N and C suggested the following COOH-terminal sequences: N, -Gly-Ser-Arg; C, -Gly-Phe. It may be concluded that N represents Cys (Cam)$^{53}$-HCS-(1-133) and C, Cys(Cam)$^{165, 182, 189}$-HCS-141-191.

Table 3

| Amino Acid Composition of Plasmic Fragments of HCS | | | | |
|---|---|---|---|---|
| | N | | C | |
| Amino Acid | Expt. | 1–133 | Expt. | 141–191 |
| Lys | 4.2 | 4 | 3.7 | 4 |
| His | 4.8 | 5 | 2.1 | 2 |
| Arg | 6.6 | 7 | 2.9 | 3 |
| SCM-Cys | 1.5 | 1 | 2.8 | 3 |
| Asp | 15.4 | 15 | 6.9 | 7 |
| Thr | 7.5 | 8 | 3.0 | 3 |
| Ser | 12.8 | 14 | 3.9 | 4 |
| Glu | 20.4 | 20 | 4.4 | 4 |
| Pro | 4.8 | 5 | 0 | 0 |
| Gly | 4.2 | 3 | 2.8 | 3 |
| Ala | 5.1 | 5 | 0.9 | 1 |
| Val | 3.9 | 4 | 3.2 | 3 |
| Met | 3.8 | 4 | 1.8 | 2 |
| Ile | 5.5 | 6 | 0 | 0 |
| Leu | 18.8 | 19 | 5.1 | 5 |
| Tyr | 4.9 | 5 | 2.9 | 3 |
| Phe | 6.8 | 7 | 4.0 | 4 |
| Trp | 0.8 | 1 | 0 | 0 |
| NH$_2$-terminal residues | Val | | $a$ | |
| COOH-terminal residue | Arg | | Phe | |

$a$ not detectable

SDS-electrophoresis gave the expected molecular weight of 5500 for the small fragment and 15,500 for the large fragment. Isoelectric focusing (pH 3.5–10) in 8 M urea gave an apparent isoelectric point of 8.6 for the small fragment and apparent isoelectric point of 5.8 for the large fragment. Native HCS under the same conditions had an apparent isoelectric point of 6.0 which is in good agreement with the values obtained experimentally.

The UV spectra in 5% acetic acid for the native hormone and the two fragments were compared. The large fragment, which contains the hormones' sole tryptophan, was virtually identical to the native hormone, other than an approximately 20% drop in intensity. The small fragment had the weak absorptions expected for phenylalanine ($\simeq$225 nm) and tyrosine ($\simeq$273 nm). When compared on a molar basis, the absorptions of the two fragments, when added together, are nearly identical to the native hormone.

The CD spectra in 5% acetic acid of native HCS and the two fragments in the region of amide bond absorption were also compared. In 5% acetic acid the noise level becomes prohibitive below 215 nm, but the native hormone and both fragments exhibited a strong band with a negative maximum at 200 nm. The spectra of the native hormone in 5% acetic acid is slightly less intense than the native hormone under basic or neutral conditions, which is expected from work previously reported. The $\alpha$-helix content calculated at 220 nm was found to be approximately 40% for the native hormone, 35% for the large fragment and 20% for the small fragment. This can be taken to indicate a relative retention of conformation for the large fragment of HCS and some loss of conformation in the small fragment.

The CD spectra of the native hormone and the two fragments in the side chain region were compared. The small fragment has only weak absorptions due to tyrosine and phenylalanine and nothing higher than 275 nm, which is as expected since this fragment lacks tryptophan. It is known that at high acetic acid concentration, the CD of HCS in the side chain region undergoes several changes. The region from 275 to 305 nm becomes progressively more negative. In 5% acetic acid, the strong negative dichroism at 285 nm decreased to some extent and the region encompassing the tyrosine and phenylalanine residues (250–275 nm) become more negative than in neutral or basic solutions. The largely altered area for the tryptophan moiety (275–300 nm) indicates that tryptophan in the large fragment is less constrained than in the native hormone.

Antisera to HCS produced a single sharp precipitin line against 10 $\mu$g of HCS. Cys(Cam)$^{53}$-HCS-(1-133) gave a weak precipitin line which showed non-identity with the native hormone. Cys (Cam)$^{165,182,189}$-HCS-(141-191) failed to give a precipitin reaction at 40 $\mu$g. Antiserum to HCS at a dilution of 1:5500 reacted with 10 ng HCS to fix about 90% complement. At the same dilution of antisera, both fragments fixed less than 10%.

The results of bioassays in the pigeon crop-sac test, summarized in Table 4, indicated that both fragments have markedly decreased in their biological acitivity. The large fragment may have low activity but is much less than the native hormone.

Table 4

| Biological Potency of Plasmic Fragments of HCS in Pigeon Crop-sac Test | | |
|---|---|---|
| Material | Total dose (mg) | Dry mucosal weight* (mg) |
| HCS | 4 | 24.2 $\pm$ 2.9 |
| | 12 | 30.5 $\pm$ 3.7 |
| N | 40 | 11.2 $\pm$ 0.7$^+$ |
| | 120 | 12.0 $\pm$ 0.9 |
| C | 120 | 6.5 $\pm$ 1.4 $^\epsilon$ |
| Saline | 0 | 8.0 $\pm$ 0.4 |

*Mean $\pm$ standard error of the mean; number of birds is indicated in parentheses.
$^+$ In comparison with the control, p value; 0.01–0.005.
$^\epsilon$ In comparison with the control, not significant.

EXAMPLE 5

Materials and Methods

Plasmin fragments of reduced-carboxamidomethylation HGH and HCS were obtained as described above. Exclusion chromatography of the reaction mixture was performed at 22° C. on a Sephadex G-100 column (1.5×60 cm) in 0.01 M $NH_4HCO_3$ of pH 8.4. For radioimmunoassay, the double-antibody procedure using a guinea pig antiserum to native HGH was performed. The growth-promoting activity was determined by the rat tibia test.

Results

Complementation reactions were carried out by adding 6.7 mg (0.43 μmol) of $Cys(Cam)^{53}$-HGH-(1-134) or $Cys(Cam)^{53}$-HCS-(1-133) in 4.9 ml of Tris HCl buffer at pH 8.4 (0.1 M, 5% (Vol/vol)butanol) to 2.7 mg (0.44 μmol) of $Cys(Cam)^{165,182,189}$-HCS-(141-191) or $Cys(Cam)^{165,182,189}$-HGH-(141-191) in 0.1 ml 1 M $NH_4OH$. Both solutions were clear before mixing and became slightly turbid after mixing. The cloudy solution was kept at 22° for 3-5 hr and then stored in the refrigerator (2°) for at least 10 days. After the removal os some insoluble material, the clear reaction mixture was submitted to exclusion chromatography on Sephadex G-100. Approximately 45% of the protein appeared in a distinct peak (designated fraction III) for recombinant I and 30% for recombinant II with a Ve/Vo ratio of 1.85. This is exactly the elution position of native HGH or HCS under the same experimental conditions.

The growth promoting activity of purified recombinants I and II are summarized in Table 5. It is evident that recombinant I had 50% potency of HGH where as II was less active in comparison with that of I.

Table 5

Growth Promoting Activity of the Recombinant Hormones by Rat Tibia Assay

| Preparation | Total dose (μg) | Response[c] |
|---|---|---|
| HGH | 20 | 242.8 ± 3.8 |
|  | 60 | 282.8 ± 1.5 |
| Recombinant I[a,d,e] | 20 | 212.0 ± 4.7 |
|  | 60 | 259.2 ± 2.9 |
| Recombinant II[b,f] | 30 | 218.5 ± 9.8 |
|  | 90 | 229.0 ± 4.1 |
| $Cys(Cam)^{53}$-HGH-(1-134) | 150 | 231.2 ± 1.6 |
|  | 450 | 275.0 ± 3.8 |
| $Cys(Cam)^{53}$-HCS-(1-133) | 300 | 185.5 ± 1.7 |
| Saline | 0 | 170.5 ± 2.1 |

[a]Recombinant I: [$Cys(Cam)^{53}$-HGH-(1-134)] + [$Cys(Cam)^{165,182,189}$-HCS-(141-191)].
[b]Recombinant II: [$Cys(Cam)$-HCS-(1-133)] + [$Cys(Cam)^{165,182,189}$-HGH-(141-191)]; the slope of dose-reponse curve is not parallel with that of HGH and relative potency cannot be calculated.
[c]Tibia width in micrometers; mean ± SEM; four animals in each group.
[d]Relative potency to HGH, 50%, with 95% confidence limit of 39-62 and λ = 0.08.
[e]Relative potency to $Cys(Cam)^{53}$-HGH-(1-134), 491% with 95% confidence limit of 398-592 and λ = 0.07.
[f]Relative potency to HGH, 10%, with 95% confidence limit of 9-12 with λ = 0.07.

The radioimmunoassay results with purified recombinants using guinea pig antiserum to HGH showed that the recombinant I at low concentrations gave nearly identical inhibition to that of HGH but the inhibition curve was not parallel with that for HGH. Although recombinant II gave a parallel inhibition curve, it was much less effective than HGH, requiring at least 30 times higher antigen concentrations to give the same degree of inhibition.

EXAMPLE 6

Protected peptide resin corresponding to peptides I-III

Boc-phenylalanyl resin (1.317 g, 0.356 mmol phenylalanine) was subjected to the following procedure: (1) washing with methylene chloride, 4×20 ml; (2) treatment with 20 ml of 55% trifluoroacetic acid-methylene chloride for 1 min; (3) treatment with 20 ml of 55% trifluoroacetic acid-methylene chloride for 15 min; (4) washing with methylene chloride, 2×20 ml; (5) washing with dioxane-methylene chloride (1:2), 3×20 ml; (6) repeat step 4; (7) treatment with 20 ml of 5% N-methylmorpholine in methylene chloride for 2 min; (8) repeat step 4; (9) repeat step 7; (10) repeat step 4; (11) treatment with 20 ml of 1% diisopropylethylamine in methylene chloride for 2 min; (12) washing with methylene chloride, 6×20 ml; (13) treatment with 1.5 mmol of the preformed symmetrical anhydride of the Boc amino acid in 14 ml of methylene chloride for 20 min; (14) addition of 0.18 mmol of N-methylmorpholine in 3 ml of trifluoroethanol to the coupling mixture and continued shaking for 20 min; (15) washing with methylene chloride, 3×20 ml; (16) washing with ethanol-methylene chloride (1:2), 3×20 ml.

$N^\alpha$ protection was by the Boc group for all amino acids. Side chain protection was as follows: Ser, O-Bzl; Thr, O-Bzl; Tyr, O-o-bromobenzyloxycarbonyl; Lys, $N^\epsilon$-o-bromobenzyloxycarbonyl; Arg, $N^G$-p-toluenesulfonyl; His, $N^{im}$-benzyloxycarbonyl; Glu, γ-benzyl ester; Asp, β-benzyl ester. Preparation of the symmetrical anhydrides of the Boc amino acids was as previously reported by Blake and Li, Int. J. Pept. Prot. Res. 7, 495 (1975) and Boc asparagine was coupled in the presence of 1-hydroxybenzotriazole. After 25 cycles of synthesis the volumes of the solvents and acid and base reagents were increased to 25 ml.

[$Nle^{170}$, $Ala^{165,182,189}$]-HGH-(145-191) (I)

A sample (503 mg, 0.050 mmol) of the peptide resin corresponding to peptide I was treated with 1.6 ml of anisole and 10 ml of liquid HF for 30 min at 0°-25° and 55 min at 0°. The HF was evaporated at 0° and the residue was stirred for 5 min with 30 ml of cold ethyl acetate. The resulting mixture was filtered, and the precipitate was washed with ethyl acetate and air dried. The precipitate was stirred for 10 min with 8 ml of 50% acetic acid; filtration gave a filtrate that was chromatographed on Sephadex G-10. Fractions corresponding to the major peak were isolated, diluted with water (1:16), and lyophylized to give 178 mg of crude peptide I. This peptide was dissolved in 20 ml of 0.5 N acetic acid and 60 ml of water was added. Ammonium hydroxide was added until the pH was 7.0. The mixture was cooled to 0°, centrifuged, and the precipitate was redissolved in dilute acetic acid and lyophilized twice to give 154 mg of peptide.

Further purification was effected by partition chromatography of 34.4 mg of peptide I on Sephadex G-50 in the system 0.52% dichloroacetic acid in sec-butanol:water:acetic acid (145:205:5). Fractions 19-26 were combined, diluted with 100 ml of water, and lyophilized almost to dryness. The still solid, nearly dry residue was dissolved in 15 ml of 0.1 M ammonium acetate, pH 9.4 (2 N sodium hydroxide was added to acid solution and then 1 N hydrochloric acid was added to return the pH to 9.4), and dialyzed against one liter of buffer for 16 h at 4°. After further dialysis against fresh buffer for 6 h, the dialysate was lyophilized to a residue that was dissolved in dilute acetic acid and relyophilized (twice) to give 12 mg of peptide. The same column was used without further washing to chromatograph an additional 37.7 mg of peptide I. Work-up as described above gave 16.2 mg of peptide which was combined with the first batch to give 28.2 mg of peptide I.

Preparative isoelectric focusing was performed on an LKB 2117-501 Ampholine Electrofocusing Kit. Sephadex G-75, superfine, (3.3 g) which had been exhaustively washed with water and ethanol and dried, was slowly added to 75 ml of 6 M urea while stirring. The slurry was poured into a 100-ml graduate cylinder and allowed to settle. When the volume of the resin bed had settled to 66 ml, the supernatant was drawn off and 2.7 ml of 40% ampholine pI 5–8 was added. The slurry was vigorously stirred with a glass rod, and allowed to settle to a volume of 64 ml. The supernatant was drawn off, the slurry was stirred again and poured onto a glass plate 24.5×11 cm×0.5 cm deep containing paper wicks at each end which had been soaked in 2% ampholine pI 5–8. The apparatus was allowed to stand overnight during which time ca. 25% of the water evaporated and the resin bed had solidified. Twenty-six milligrams of peptide I, which had been purified by partition chromatography, was dissolved in 1 ml of 8 M urea. Then, using a sample applicator, a band of the Sephadex bed 2 cm wide and ca. 2 cm from the anode end was scooped out with a spatula and mixed with the urea solution of peptide. The resulting thick slurry was poured back onto the plate, the sample applicator was removed, and with the acid of a spatula and additional urea solution, the sample band was made to coalesce with the resin bed. An additional paper wick soaked in 1 M phosphoric acid and 2 M potassium hydroxide was placed on top of the ampholine-soaked wicks at the anode and cathode end, respectively. The electrodes were attached and the Sephadex bed was subjected to a potential of 300 V for 2 h and 600 V for 4 h. At this time a paper print was taken by laying a piece of Whatman 3 MM paper over the top of the Sephadex bed. Visualization of peptide bands by staining in Bromophenol blue showed a major band centered 8.2 cm from the anode. The region corresponding to the major band was scraped off with the aid of a spatula, and washed with 3 ml of 10% acetic acid. The mixture was filtered, and the Sephadex was further washed with 1.5 ml of 10% acetic acid. The combined washings were chromatographed on Sephadex G-100 in 0.5 N acetic acid/1 mM ammonium acetate to give 5.2 mg of peptide I (4.6% yield based on starting Boc-Phe resin). Thin-layer chromatography on silica gel in the system n-butanol:-pyridine:acetic acid:water (5:5:1:4) (BPAW) gave a single ninhydrin, chlorine positive spot at $R_f$ 0.41. Analysis of the amino terminal amino acid by the dansyl method showed only lysine. Amino acid analysis of an acid hydrolysate of peptide I is indicated in Table 6.

TABLE 6

| Amino acid analyses of the synthetic peptides | | | | | |
|---|---|---|---|---|---|
| Peptide I | | Peptide II | | Peptide III | |
| Theory | Found | Theory | Found | Theory | Found |
| Lys | 4 | 3.9 | 5 | 4.8 | 8 | 8.4 |
| His | 1 | 1.0 | 1 | 1.0 | 1 | 1.0 |
| Arg | 3 | 3.0 | 3 | 3.0 | 3 | 3.2 |
| Asp | 8 | 8.1 | 8 | 8.2 | 8 | 8.4 |
| Thr | 2 | 2.1 | 3 | 2.8 | 3 | 3.0 |
| Ser | 3 | 2.6 | 4 | 3.6 | 4 | 3.7 |
| Glu | 3 | 3.0 | 4 | 4.3 | 6 | 6.2 |
| Gly | 3 | 2.9 | 3 | 3.1 | 3 | 3.1 |

TABLE 6-continued

| Amino acid analyses of the synthetic peptides | | | | | |
|---|---|---|---|---|---|
| Peptide I | | Peptide II | | Peptide III | |
| Theory | Found | Theory | Found | Theory | Found |
| Ala | 4 | 3.8 | 4 | 4.0 | 4 | 4.0 |
| Val | 3 | 2.7 | 3 | 2.7 | 3 | 2.8 |
| Ile | 1 | 0.9 | 1 | 0.8 | 1 | 0.8 |
| Leu | 5 | 5.0 | 5 | 5.0 | 5 | 5.0 |
| Nle | 1 | 1.0 | 1 | 0.9 | 1 | 1.0 |
| Tyr | 2 | 1.9 | 3 | 2.9 | 3 | 3.0 |
| Phe | 4 | 4.0 | 4 | 3.9 | 4 | 4.2 |

[Nle$^{170}$, Ala$^{165,182,189}$]-HGH-(140-191) (II)

Peptide II was purified as described for peptide I, except that preparative isoelectric focusing was effected on polyacrylamide gel. thus, 556 mg (0.042 mmol) of peptide resin gave 208 mg of crude peptide II as isolated after chromatography on Sephadex G-10. Isoelectric precipitation as described for peptide I have 179 mg of peptide. Partition chromatography, in two portions, of 100.8 mg on Sephadex G-50 gave 41 mg of peptide II ($R_f$ 0.41). For preparative isoelectric focusing nine cyclindrical gels (1.45×9.6 cm) were used. Polyacrylamide gels were made by the polymerization of a solution of 5.1% acrylamide, 0.9% diallytartardiamide, 2% ampholine pI 5–8, 0.06% ammonium persulfate, 0.002% riboflavin, and 0.05% tetramethylenediamine in 8 M urea. Peptide II (18.9 mg) was dissolved in 2.2 ml of 10 M urea and then 100 μl of 40% ampholine pH 5–8 was added. One-ninth of the peptide solution was added to the top of each of the gels and the gels were subjected to a constant current of 20 ma for 20 min, and a constant voltage of 100 V for 8 h. For detection of peptide, one of the gels was allowed to stand in 15% trichloroacetic acid and after 30 min the major band was visible. The portion of the gel corresponding to the region of the major band was cut out of the remaining eight gels. The gel slices were further minced with the aid of a razor blade, added to 100 ml of 15% acetic acid, and the mixture was stirred at 4° for 16 h. After filtration and further washing of the gel, the filtrate was dialyzed against 4 liters of 2% acetic acid for 4 h, and 2 liters of 2% acetic acid for 3 h. The dialysate was lyophilized and the residue was chromatographed on Sephadex G-100 in 0.5 N acetic acid/1 mM ammonium acetate to give 2.4 mg of highly purified peptide II (3.7% yield based on starting Boc-Phe resin). Thin layer chromatography in BPAW gave a single ninhydrin, chlorine positive spot at $R_f$ 0.44. Analysis of the amino terminal amino acid by the dansyl method showed only lysine. A sample of the peptide was submitted to isoelectric focusing on polyacrylamide gel. Amino acid analysis of an acid hydrolysate of peptide II is indicated in Table 6.

[Lys$^{135,136,138}$, Glu$^{137,139}$, Nle$^{170}$,Ala$^{165,182,189}$]-HGH-(135-191) (III)

Peptide III was isolated from the peptide resin in the same manner as described for peptide I, except that no attempt at isoelectric precipitation was made. Thus 505 mg (0.036 mmol) of peptide resin gave 167 mg of crude peptide III as isolated after chromatography on Sephadex G-10. Partition chromatography, in two portions, of 75.5 mg of peptide on Sephadex G-50 in the system 0.52% trichloroacetic acid in sec-butanol:0.03 N HCl:acetic acid (145:205:5) gave 26.1 mg of peptide III ($R_f$ 0.29). Further purification was affected by preparative isoelectric focusing of 19 mg of peptide III as described for peptide I, except that ampholine pI 7–9 was used, to give 3.8 mg of highly purified peptide III (4.7% yield based on starting Boc-Phe resin). Thin-layer chromatography in BPAW gave a single ninhydrin, chlorine positive spot at $R_f 0.21$. Analysis of the amino terminal amino acid by the dansyl method showed only lysine. A sample of the peptide was submitted to isoelectric focusing on polyacrylamide gel. Amino acid analysis of the acid hydrolysate of peptide III is indicated in Table 6.

The growth promoting activity for peptides I–III is summarized in Table 7.

TABLE 7

Growth-promoting activity of synthetic HGH fragment analogs assayed by the rat tibia test

| Preparation | Response[a] | P values vs Saline | P values vs Natural peptide |
|---|---|---|---|
| Natural[Cys(Cam)$^{165,182,189}$]-HGH-(141-191) | 212 ± 7.3 | <0.001 | |
| [Nle$^{170}$, Ala$^{165,182,189}$]-HGH-(140-191) | 197 ± 4.2 | <0.001 | >0.1<0.2 |
| [Lys$^{135,136,138}$, Glu$^{137,139}$, Nle$'^{70}$, Ala$^{165,182,189}$]-HGH-(135-191) | 192 ± 3.5 | <0.001 | <0.05>0.025 |
| [Nle$'^{70}$, Ala$^{165,182,189}$]-HGH-(145-191) | 189.5 ± 7.5 | <0.025 >0.01 | >0.1<0.05 |
| Saline | 167 ± 1.3 | | |

[a]Means ± S.E. in microns. Each response is calculated from four test animals. Each animal received a total dose of 600 μg of natural or synthetic peptides in 4 days.

Complementation reactions were performed using 0.43 nmole each of the NH$_2$-terminal fragment [Cys(Cam)$^{53}$]-HGH-(1-134) and the synthetic analogs of the COOH-terminal fragment (Nle$^{170}$, Ala$^{165,182,189}$)-HGH-(145-191) and (Nle$^{170}$, Ala$^{165,182,189}$)-HGH-(140-191) as described in Example 5. The elution pattern of the reaction mixture was obtained on Sephadex G-100. It may be noted that approximately 45% of the material appears in peak III at a Ve/Vo ratio of 2.12 for [Cys(Cam)$^{53}$]-HGH-(1-134)+(Nle$^{170}$, Ala$^{165,182,189}$)-HGH-(145-191) (recombinant III) and 30% for [Cys(Cam)$^{53}$]-HGH-(1-134)+(Nle$^{170}$, Ala$^{165,182,189}$)-HGH-(145-191) (recombinant IV). The elution positions of the two recombinants are the same for HGH under identical experimental conditions. The recovered protein from peak III was assyed for growth-promoting activity and the results are summarized in Table 8.

Table 8

Growth-Promoting Activity of Recombinant Hormones by Rat Tibia Assay

| Preparation | Total dose (μg) | Response[a] |
|---|---|---|
| HGH | 20 | 245.0 ± 9.5 |
| | 60 | 290.2 ± 2.9 |
| Recombinant III[b,d] | 20 | 249.2 ± 9.2 |
| | 60 | 286.0 ± 2.1 |
| Recombinant IV[c,e] | 20 | 248.5 ± 7.7 |
| | 60 | 297.2 ± 10.0 |
| Saline | 0 | 167.0 ± 1.3 |

[a]Tibia width in micrometers: mean ± SEM; four animals in each group.
[b]Recombinant III: [Cys(Cam)$^{53}$]-HGH-(1-134) + [Nle$^{170}$, Ala$^{165, 182, 189}$]-HGH-(140-191).
[c]Recombinant IV: [Cys(Cam)$^{53}$]-HGH-(1-134) + [Nle$^{170,}$ Ala$^{165, 182, 189}$]-HGH-(145-191).
[d]Relative potency to HGH, 100%, with 95% confidence limits of 65–154 and λ = 0.16.
[e]Relative potency to HGH, 113%, with 95% confidence limits of 74–180 and λ = 0.16.

It is evident that both recombinants exhibit full somatotropic activity in comparison with the native hormone.

Radioimmunoassay of the recombinants showed a strong cross-reaction which was almost identical to that of the native HGH standard at low concentrations whereas the NH$_2$-terminal [Cys(Cam)$^{53}$]-HGH-(1-134) gave only a slight cross-reaction.

EXAMPLE 7

Prolactin was isolated from sheep pituitary glands by the procedure previously described. Bacterial fibrinolysin (esterase-free) was obtained from Calbiochem. Prolactin (100 mg) was digested with fibrinolysin in 50 mM ammonium acetate (pH 8.0) with an enzyme to substrate ratio of 1:100 (wt/wt) at 21° for 9 hr. The digest was submitted to gel filtration on a Sephadex G-75 column (2.5×150 cm) in 20% acetic acid with a flow rate of 10 ml/hr. The isolated fragments were lyophilized and rechromatographed under the same conditions. The fragments were further purified by gel filtration on Sephadex G-100 in 10 mM NH$_4$HCO$_3$ (ph 8.4). Digestions with carboxypeptidase A (Worthington) were carried out in 0.1 M NaHCO$_3$ with an enzyme to peptide ratio of 1:10 (wt/wt) for 15 hr at 37°. Amino acid composition of acid and carboxypeptidase hydrolysates were determined in an automatic amino acid analyzer. For the analysis of tryptophan, hydrolysis with methanesulfonic acid was used. Amino-terminal residue and sequence analyses were performed by the dansyl-Edman procedures. Disc electrophoresis in polyacrylamide gel (7%) was carried out in Tris-glycine buffer (pH 8.3) for 60 min at 100 V with a current of 4 mA per tube (7.5×0.5 cm). The gels were stained with Amido Black and destained by electrophoresis in 7% acetic acid.

Exclusion chromatography of the purified fragments or the recombinant was performed on a Sephadex G-100 column (1.5×60 cm; V$_0$=35 ml) in 10 mM NH$_4$HCO$_3$ (pH 8.4) at 21°. Circular dichroism (CD) spectra were obtained by a spectropolarimeter (Cary model 60) equipped with a circular dichroism attachment (model 6002). Microcomplement fixation was performed with the guinea pig antiserum to ovine prolactin. The gel double-diffusion technique of Ouchterlony was carried out with 1% agar in 10 mM phosphate buffer (pH 7.5). The prolactin activity was estimated by the local crop-sac assay in the pigeon.

Prolactin gives rise to two main components, I and II, with one minor component, III, in disc electrophoresis. The digestion with fibrinolysin converted major portions of the hormone into two faster moving components, III and IV. Fractions of the digest, which had been separated on the Sephadex G-75 column, were pooled. Polyacrylamide gel electrophoresis showed that fraction α contained undigested prolactic, fraction β contained mainly the faster moving components III and IV, which were still accompanied by prolactin, but fraction γ was free of the native hormone. Rechromatography of fraction β, under the same experimental conditions, led to full separation of components III and IV from the native prolactin.

End-group analyses of the different fractions revealed that, except for the undigested prolactin, only fractions γ and C had single NH$_2$-terminal residues: γ, Ala, and C, Thr. These two fractions were further purified by exclusion chromatography on Sephadex G-100. From 200 mg of ovine prolactin, average yields of highly purified and C were 30 mg and 10 mg, respectively. The highly purified γ and C fractions were submitted to terminal sequence analyses and gave the following results: γ, Ala-Leu-Asx- and C, Thr-Pro-Val-. Liberation of amino acids from carboxypeptidase A digest of C provided evidence for the COOH-terminal sequence -Ile-Thr-Met, whereas no amino acid was liberated by carboxypeptidase A or B digestion of γ. These findings, together with the amino acids composition summarized in Table 8 led to the conclusion that the major site of cleavage of prolactin by fibrinolysin is the Met-Ala bond at positions 53-54 and that the main product of this limited proteolysis is composed of the NH$_2$-terminal portion, residues 1-53 [fragment C, henceforth PRL-(1-53)] and the COOH-terminal portion, residues 54-199 [fragment γ, henceforth PRL-(54-199)] of ovine prolactin.

Table 9

Amino acid composition* of fragments from ovine prolactin obtained by limited proteolysis with fibrinolysin

| Amino acid | Prolactin † | γ Exp. | 54-199 ‡ | C Exp. | 1-53 ‡ |
|---|---|---|---|---|---|
| Lys | 9 | 7.2 | 7 | 1.8 | 2 |
| His | 8 | 5.9 | 6 | 1.9 | 2 |
| Arg | 11 | 7.8 | 8 | 2.7 | 3 |
| Asx | 22 | 15.5 | 15 | 7.2 | 7 |
| Thr | 9 | 7.0 | 7 | 2.1 | 2 |
| Ser | 15 | 10.5 | 11 | 3.6 | 4 |
| Glx | 22 | 18.5 | 18 | 3.7 | 4 |
| Pro | 11 | 8.3 | 8 | 3.3 | 3 |
| Gly | 11 | 7.1 | 7 | 4.2 | 4 |
| Ala | 9 | 7.0 | 7 | 1.9 | 2 |
| ½Cys | 6 | 3.5 | 4 | 1.8 | 2 |
| Val | 10 | 5.6 | 6 | 4.4 | 4 |
| Met | 7 | 3.8 | 4 | 2.6 | 3 |
| Ile | 11 | 8.3 | 9 | 1.6 | 2 |
| Leu | 23 | 20.5 | 20 | 3.4 | 3 |
| Tyr | 7 | 4.7 | 5 | 1.8 | 2 |
| Phe | 6 | 2.2 | 2 | 4.0 | 4 |
| Trp | 2 | 1.7 | 2 | 1.8 | 0 |

*Molar ratios.
† Taken from refs. 1 and 2.
‡ Residue position in the ovine prolactin structure Sodium dodecyl sulfate electrophoresis analyses indicated molecular weights of ~17,500 for PRL-(54-199) and of less than 7000 for PRL-(1-53).

Exclusion chromatography on Sephadex G-100 suggested a dimeric product (molecular weight ≈37,000) for PRL-(54-199) and a monomeric form (molecular weight <8000) for PRL-(1-53).

The CD spectra of PRL-(54-199)(mean residue weight 114.1) and PRL-(1-53)(mean residue weight 113.2) were examined. The positive maximum around 296-298 nm, which is typical for native prolactin in the region of side-chain absorption, has completely disappeared. It is of interest to point out the appearance of a negtive band 297 nm in the spectrum of PRL-(54-199). The strong negative band at 223 nm, characteristic of the amide bond CD spectrum of ovine prolactin was considerably weaker for both fragments whereas the second band around 209 nm became relatively stronger than that at 223 nm, indicating that both fragments possess considerable α-helical content.

The recombinant of the two fragments was prepared by dissolving 1.6 mg (0.1 μmol) of PRL-(54-199) and 1.2 mg (0.2 μmol) of PRL-(1-53) in 1 ml of 0.1 M Tris HCl buffer (pH 8.2), yielding a clear solution. The CD spectrum was taken immediately. The mean residue ellipticities were calculated using 113.9 as the mean residue molecular weight for the mixture of the two fragments. The spectrum of the recombinant differs markedly from the individual spectra of the fragments and is by no means the summation of the two. The interesting feature of the spectrum of the recombinant is the appearance of the positive maximum around 296-298 nm, which is typical for the natural hormone. The appearance of a shoulder around 288 nm and strong negative bands at 223 nm may also be noted. The latter may suggest that the α-helical content of the recombinant is identical to or somewhat higher than that of the natural hormone. However, minor differences could be noted between the natural hormone and the recombinant around 288 nm and in the region of 265-275 nm.

The noncovalent recombination of PRL-(1-53) and PRL-(54-199) to a prolactin-like recombinant was further shown by its behavior in exclusion chromatography on Sephadex G-100.

The recombinant emerged as a single symmetrical peak with $V_e/V_0 = 2.03$, which is identical to that for the natural hormone.

Immunological studies also indicated that PRL-(1-53) and PRL-(54-199) recombined noncovalently to form a product that was indistinguishable from the natural hormone. Antiserum to prolactin produced a single precipitin line against the recombinant and the natural hormone, indicating identity to each other, whereas neither fragment gave a precipitin line.

Guinea pig antiserum to ovine prolactin at a dilution of 1:5000 reacted with 10 ng of the antigen to fix 98% of complement, and the recombinant behaved nearly identically. Both fragments fixed less than 10% of complement.

Table 10 presents the biological activity of the recombinant as assayed by the pigeon crop-sac test. Since the slopes of dose-response curves for prolactin and the recombinant are different, it is impossible to complete quantitatively the relative potency. However, it may be estimated that the recombinant possesses approximately 2% the activity of the natural hormone while the fragments each individually were devoid of biological activity.

Table 10

Lactogenic activity of prolactin, fragments, and recombinant in the pigeon crop-sac assay

| Preparations | Total dose, μg | Response* |
|---|---|---|
| Prolactin | 2 | 20.5 ± 0.9 (5) |
| | 6 | 45.2 ± 3.1 (5) |
| PRL-(1-53) | 120 | 10.1 ± 2.6 (4) |
| PRL-(54-199) | 120 | 12.2 ± 3.0 (4) |
| Recombinant | 6 | 8.1 ± 1.5 (4) |
| PRL- (1-53) + | 20 | 9.0 ± 0.8 (4) |
| PRL- (54-199) | 120 | 18.7 ± 1.3 (8) |
| Saline | 0 | 7.0 ± 0.6 (4) |

*Dry mucosal weight in mg; mean ± SEM, number of birds in parentheses.

EXAMPLE 8

Equimolar amounts of [Cys(Cam)$^{53}$]-HCS-(1-33) and each of the following HGH amino terminal analogs:
 (Nle$^{170}$, Ala$^{165,182,189}$)-HGH-(140-191)
 (Lys$^{135,136,138}$, Glu$^{137,139}$, Nle$^{170}$, Ala$^{165,182,189}$)-HGH-(135-191)
 (Nle$^{170}$, Ala$^{165,182,189}$)-HGH-(145-191)
are subjected to the non-covalent complementation conditions described in Example 5 so as to produce the following recombinant compounds:
 [Cys(Cam)$^{53}$]-HCS-(1-133)+(Nle$^{170}$, Ala$^{165,182,189}$)-HGH-(135-191);
 [Cys(Cam)$^{53}$]-HCS-(1-133)+(Lys$^{135,136,138}$, Glu$^{137,139}$, Nle$^{170}$,Ala$^{165,182,189}$)-HGH-(135-191); and
 [Cys(Cam)$^{53}$]-HCS-(1-133)+(Nle$^{170}$,Ala$^{165,182,189}$)-HGH-(145-191).

The aforesaid recombinant compounds exhibit analogous conformational, immunological and biological activity as native HGH and HCS.

EXAMPLE 9

Equimolar amounts of [Cys(Cam)$^{53}$]-HGH-(1-134) and (Lys$^{135,136,138}$, Glu$^{137,139}$, Nle$^{170}$, Ala$^{165,182,189}$)-HGH-(135-191) are subjected to the non-covalent complementation conditions described in Example 5 so as to produce the recombinant compound [Cys(Cam)$^{53}$]-HGH-(1-134)+(Lys$^{135,136,138}$, Glu$^{137,139}$, Nle$^{170}$, Ala$^{165,182,189}$)-HGH-(135-191). The aforesaid recombinant compound exhibits analogous conformational, immunological and biological activity as native HGH.

I claim:

1. A recombinant composition having essentially the equivalent conformation, immunoreactivity and biological activity of a single chain peptide hormone selected from the group consisting of human growth hormone, human chorionic somatomammotropin and prolactin having a molecular weight of greater than about 5,000, said composition containing two peptide fragments in non-covalent complementation relationship to each other and said peptide fragments each having a sequence corresponding to a different portion of said peptide hormone.

2. The recombinant composition of claim 1 wherein said peptide hormone is human chorionic somatomammotropin and said peptide fragments are [Cys(Cam)$^{53}$]-HCS-(1-133) and [Cys(Cam)$^{165,182,189}$]-HCS-(141-191).

3. The recombinant composition of claim 1 wherein said peptide hormone is prolactin and said peptide fragments are PRL-(1-53) and PRL-(54-199).

4. A recombinant composition having essentially the equivalent conformation and biological activity of human growth hormone said composition containing two peptide fragments in non-covalent complementative relationship to each other and said peptide fragments each having a sequence corresponding to a different portion of said human growth hormone.

5. The recombinant composition of claim 4 wherein the peptide fragments present do not in combination contain the total amino acid content of said human growth hormone.

6. The recombinant composition of claim 5 wherein said peptide fragments are [Cys(Cam)$^{53}$]-HGH-(1-134) and [Cys(Cam)$^{165,182,189}$]-HGH-(141-191).

7. The recombinant composition of claim 5 wherein said peptide fragments are [Cys(Cam)$^{53}$]-HGH-(1-134) and [Cys(Cam)$^{165,182,189}$]-HCS-(141-191).

8. The recombinant composition of claim 5 wherein said peptide fragments are [Cys(Cam)$^{53}$]-HCS-(1-133) and [Cys(Cam)$^{165,182,189}$]-HGH-(141-191).

9. The recombinant composition of claim 5 wherein said peptide fragments are [Cys(Cam)$^{53}$]-HGH-(1-134) and a fragment selected from the group consisting of (Nle$^{170}$, Ala$^{165,182,189}$)-HGH-(140-191), (Lys$^{135,136,138}$, Glu$^{137,139}$, Nle$^{170}$, Ala$^{165,182,189}$)-HGH-(135-191) and (Nle$^{170}$, Ala$^{165,182,189}$)-HGH-(145-191).

10. The recombinant composition of claim 5 wherein said peptide fragments are [Cys(Cam)53]-HCS-(1-133) and a fragment selected from the group consisting of (Nle$^{170}$, Ala$^{165,182,189}$)-HGH-(140-191), (Lys$^{135,136,138}$, Glu$^{137,139}$, Nle$^{170}$, Ala$^{165,182,189}$)-HGH-(135-191) and (Nle$^{170}$, Ala$^{165,182,189}$)-HGH-(145-191).

11. a method for preparing a recombinant composition having essentially the equivalent conformation and biological activity of human growth hormone which method comprises mixing two peptide fragments, which peptide fragments each have a sequence corresponding to a different portion of said human growth hormone, in aqueous buffer of a pH in the range of from 6 to 10 so as to produce a non-covalent complementation of said fragments.

12. The method of claim 11 wherein said aqueous buffer also contains a minor amount of a C$_{1-4}$ alkanol.

13. The method of claim 12 wherein said buffer is pH 8.4 tris buffer and said C$_{1-4}$ alkanol is n-butanol.

14. PRL-(1-53).

15. PRL-(54-199).

16. (Nle$^{170}$, Ala$^{165,182,189}$)-HGH-(140-191).

17. (Lys$^{135,136,138}$, Glu$^{137,139}$, Nle$^{170}$, Ala$^{165,182,189}$)-HGH-(135-191).

18. (Nle$^{170}$, Ala$^{165,182,189}$)-HGH-(145-191).

* * * * *